US011129663B2

(12) United States Patent
Barken (10) Patent No.: US 11,129,663 B2
(45) Date of Patent: Sep. 28, 2021

(54) HIGH-TEMPERATURE CRYOSURGERY SYSTEM AND METHODS OF USING THE SAME

(71) Applicant: Israel Barken, San Diego, CA (US)

(72) Inventor: Israel Barken, San Diego, CA (US)

(73) Assignee: Israel Barken, San Diego, CA (US)

( * ) Notice: Subject to any disclaimer, the term of this patent is extended or adjusted under 35 U.S.C. 154(b) by 0 days.

(21) Appl. No.: 17/033,269

(22) Filed: Sep. 25, 2020

(65) Prior Publication Data
US 2021/0145500 A1   May 20, 2021

Related U.S. Application Data

(60) Provisional application No. 62/907,452, filed on Sep. 27, 2019.

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00199* (2013.01); *A61B 2018/00714* (2013.01);
(Continued)

(58) Field of Classification Search
CPC .......... A61B 18/02; A61B 2018/00714; A61B 2018/00761; A61B 2018/00791; A61B 2018/0262; A61B 2018/0293
See application file for complete search history.

(56) References Cited

U.S. PATENT DOCUMENTS

| 4,018,227 A | * | 4/1977 | Wallach | ................. | A61B 18/02 606/23 |
| 2003/0018326 A1 | * | 1/2003 | Abboud | ................. | A61B 18/02 606/20 |

(Continued)

*Primary Examiner* — Daniel W Fowler
(74) *Attorney, Agent, or Firm* — David G. Rosenbaum; Rosenbaum IP (57) ABSTRACT

A high temperature cryosurgery system and method of operation comprising a refrigeration assembly, a cryoprobe and a refrigerant wherein the cryoprobe and the refrigeration assembly are fluidly coupled in a closed loop configured to cycle the refrigerant in a fluid state from the refrigeration assembly to the cryoprobe and further configured to cycle the refrigerant in a vapor state from the cryoprobe to the refrigeration assembly. A method for treating cancer tumors and metastatic cancer cells by disrupting the tumor by sequentially or concurrently administering an ablative energy in combination with immunomodulation and/or pharmacological application, in one or more cycles, where the physical disruption is applied at levels sufficient to create the abscopal effect. That effect is generated by stimulating the immune cells in the microenvironment. The tumor is treated in a way permitting the remaining cells or elements in the tumor microenvironment to exert net immune stimulation with also long-term memory cells to fight subsequent appearing tumor in the future. Adding immune modulators injected in situ systemically or embedded in slow releasing means locally or systemically will boost the immune response to the cancer.

16 Claims, 2 Drawing Sheets

(52) U.S. Cl.
CPC ........... *A61B 2018/00761* (2013.01); *A61B 2018/00791* (2013.01); *A61B 2018/0262* (2013.01); *A61B 2018/0293* (2013.01)

(56) References Cited

U.S. PATENT DOCUMENTS

| | | | |
|---|---|---|---|
| 2004/0000158 A1* | 1/2004 | Luo | F25B 19/005 62/259.3 |
| 2004/0158237 A1* | 8/2004 | Abboud | A61B 18/02 606/21 |
| 2005/0090814 A1* | 4/2005 | Lalonde | A61B 18/02 606/22 |
| 2008/0140061 A1* | 6/2008 | Toubia | A61B 18/02 606/20 |
| 2013/0296837 A1* | 11/2013 | Burnett | A61B 17/12022 606/21 |

* cited by examiner

HIGH-TEMPERATURE CRYOSURGERY SYSTEM AND METHODS OF USING THE SAME

BACKGROUND

The invention generally relates to cryosurgery. More particularly the invention relates to a closed loop cryosurgery system comprising a cooling or refrigeration assembly, an operator cooling probe, a refrigerant and operation thereof.

Cryosurgery is the use of extreme cold in surgery to ablate or destroy abnormal or diseased tissue; thus, it is the surgical application of cryoablation. Cyrosurgery typically involves spraying fluid nitrogen, carbon dioxide, argon, or a mixture of dimethyl ether and propane directly on the tissue, dabbing it on a cotton swab and swabbing the effected tissue areas, or using a probe or needle which is cooled and then applied directly on the effected tissue. Such probes or needles are referred to herein as "cryoprobes" or "cryoneedles," respectively and the terms are used interchangeably except where the context indicates otherwise.

In some instances, cryosurgery is used to treat internal and external tumors as well as tumors in the bone. To cure internal tumors, a hollow instrument called a cryoprobe is used, which is placed in contact with the tumor. Fluid nitrogen or argon gas is passed through the cryoprobe. Ultrasound or MRI is used to guide the cryoprobe and monitor the freezing of the cells. This helps in limiting damage to adjacent healthy tissues. A ball of ice crystals forms around the probe which results in freezing of nearby cells. After cryosurgery, the frozen tissue is either naturally absorbed by the body in the case of internal tumors, or it dissolves and forms a scab for external tumors.

Conventional cryosurgery systems typically operate at about −185 degrees Celsius at the tip of the cryoneedle during the treatment. These temperatures typically result in the complete ablation of both the treated tissue, e.g., a tumor, and the surrounding micro-environment. In contrast, the present invention provides a high temperature cryoablation system which is configured to incompletely ablate treated tissue at temperatures higher than such conventional cryosurgery systems, e.g., between about 0 degrees Celsius to about −80 degrees Celsius. Such higher temperature cryoablation, in accordance with the present invention, enables partial ablation of the treated tissue, e.g., tumor cells, without collateral damage to the tumor micro-environment. This enables the tumor micro-environment to marshal the body's native immune system to attack and destroy remaining local or systemic cancer cells.

The inventive cryosurgical system may be used in surgical methods for treatment of a cancer tumor and, in particular, to a surgical method that purposely removes or ablates initially only a portion of an identified tumor and, subsequently, attacks the tumor more by stimulating the body's native immune response with the lysed tumor cell contents and/or adding additional therapeutic modalities that elicit the body's native immune responses to eliminate the cancer. Despite a medical research war waged for decades, cancer remains a major killer today. There are well over 1.6 million new cases of the four major cancers (colorectal, lung and bronchus, breast and prostate cancers) each year in both men and women, with over 500,000 deaths estimated from these cancers each year. Pancreatic cancer also accounts for 3% of all cancers annually and is the fourth leading cause of cancer mortality. Similarly, brain cancer has low five-year survival rates of about 35%. Where a cancer involves a solid tumor, common approaches involve chemical or radiological methods for shrinking the tumor in combination with surgery for its removal, to the extent possible.

Conventional cryosurgery entails ablating tumor tissue by freezing the tumor tissue at a temperature and for a period of time sufficient to cause tumor cell death. Cryosurgery is an accepted mode of treatment for a variety of solid tumors, including retinoblastoma, early-stage skin cancers, bone cancers, prostate cancer, lung cancer, renal cancer, breast cancer, pancreatic cancer, liver cancer, and brain tumors.

The aim of conventional cryosurgery is to destroy as much tumor tissue as possible with little or no damage to surrounding normal tissue, i.e., the microenvironment surrounding the tumor tissue. However, even with more readily treated cancers, where the great majority of patients have greater than five-year survival rates, better methods are needed to further increase patient survival and quality of life. The present invention is directed to that goal, with particular focus on solid tumor cancers and those that have metastatic disease. By changing the cryosurgery modality from complete tumor destruction to an incomplete or sub-total tumor destruction modality that releases cellular contents from lysed tumor cells, the abscopal effect is activated by the released tumor cellular contents and activates the native immune system to eliminate the remaining surviving tumor cells both locally and systemically.

Incomplete or subtotal tumor destruction may be achieved by relatively higher temperature freezing, e.g., between about 0 to about −80 degrees Celsius, to the tumor. The resulting effect on the tumor combined with the enabling tumor microenvironment activity which is not destroyed cryosurgery activates the abscopal effect as described by Ngwa, W., et al, *Nature Reviews Cancer* 18: 313-322 (2018). The incomplete or subtotal tumor destruction will also activate a class of immune cells carrying cellular information about the tumor cells that will then be equipped to fight any resurfacing tumor cells in the future post treatment.

Without intending to be bound by theory, it is believed that by not freezing the tumor completely to destruction, the body's immune system is mobilized to approach the tumor information and mount an attack on the tumor locally, systematically and future surfacing metastatic disease. Achieving this goal is done by geographically not destroying all tumor cells by applying a less destructive force to the targeted tumor, such as by high temperature cryoablation or other attenuated methodologies for disrupting the tumor and incompletely destroying the tumor cells. Historically, in cryoablation the temperature is brought down to −185 Celsius which typically destroys both the tumor and the tumor micro-environment, i.e., healthy cells in regions around the tumor. Higher temperature cryoablation, between about 0 to about −80 degrees Celsius will enable partial destruction of the tumor cells without damage to the tumor micro-environment and enable the tumor micro-environment to marshal the body's native immune system to attack and destroy remaining local or systemic cancer cells.

SUMMARY OF THE INVENTION

Disclosed herein are cryoablation systems, methods and apparatuses. A first embodiment of the system comprises a refrigeration assembly, an operator probe, and fluid refrigerant cycling through the refrigeration assembly, and cooling cryoprobe in a closed loop. The operator probe consists generally of a housing defining interior fluid chambers for fluid phase refrigerant and vapor phase refrigerant, a cryoneedle projecting from the housing and in thermal communication with the interior fluid chambers of the housing, and fluid conduits in fluid flow communication with the interior fluid chambers. The cryoneedle may be at least partially hollow to accommodate a thermocouple and is in thermal communication with both the fluid phase and vapor phase refrigerant within the housing. In this manner a fluid loop is created between the refrigeration assembly and the operator probe in which the refrigerant fluid is recycled between the refrigeration assembly and the operator probe through the fluid conduits. When the cryoprobe is in contact with or proximity to tissue to be treated, the fluid refrigerant enters the cryoprobe chamber through an inlet fluid conduit, cools the cryoneedle, and then undergoes a phase change into vapor as the cryoneedle conducts heat away from targeted tissue, organs or bone. The vapor exits an interior fluid chamber within the operator probe housing, is returned, through an outlet fluid conduit, to the refrigeration assembly, and is converted back into a fluid for recycling within the fluid loop.

The cryoprobe temperature may be adjusted by adjusting the compressor to provide additional cooling to the refrigerant itself. In some embodiments, adjusting the position of the cryoprobe may account for small temperature variations of up to 10° C.

The refrigeration assembly comprises a vapor intake conduit configured to relay refrigerant vapors from the cryoprobe chamber through a sub-cooling device, through a compressor, through a condenser configured to condense the refrigerant vapors into fluid, through a fluid conduit, through the sub-cooling device, and out to the cryoprobe chamber.

The cryoprobe chamber comprises a fluid refrigerant chamber having a fluid refrigerant intake coupled to the refrigeration assembly, a vapor fluid separator member, a vapor mix chamber having a vapor exhaust coupled to the refrigeration assembly, a cryoprobe having a body partially disposed in fluid refrigerant chamber and partially disposed in the vapor mix chamber, and a cryoneedle tip configured to project outside of the vapor mix chamber.

In another aspect of the invention the fluid chamber further comprises a main refrigerant fluid chamber configured to accommodate the cryoprobe, and an excess fluid chamber configured to store excess refrigerant.

In another aspect of the invention, the cryoprobe comprises fixation adjustment points disposed along the body of the cryoprobe configured to accommodate a fastener coupled to the operator cooling probe. In this embodiment, the cryoprobe tip may be extended away from, or retracted into, the body of the operator cooling probe and be fixed in position through the fasteners and fixation adjustment points. In some embodiments, the fixation adjustment points may be holes and the fasteners may be retractable fixation pins.

In yet another aspect of the invention, the cryoprobe further comprises a thermocouple coupled to the body of the cryoprobe configured to measure the temperature of the needle. In some embodiments, the cryoprobe may further comprise multiple thermocouples to read the temperature of various portions of the cryoprobe body. In other embodiments, the cryoprobe may comprise a hollow body having the thermocouple disposed within and placed at a predetermined distance from the cryoprobe tip. The thermocouple may be coupled to a digital display or a computing device configured to read and report the thermal data to the end user. In another arrangement, the cryoprobe probe may have a lumen to inject substances into the tumor.

In yet another aspect of the invention, a computing device coupled to the thermocouple further comprises and operating system and graphical user interface pre-configured or customizable with temperature configurations required for selected surgeries. In this embodiment, the system may alert the user if the temperature is too high or too low for the particular surgery and automatically adjust the compressor or needle position or prompt the user to adjust the compressor to attain the proper temperature.

In yet another aspect of the invention, a method of using the cryosurgery system comprises the steps of cycling fluid refrigerant through the refrigeration assembly into the cryoprobe fluid chamber, cooling the cryoprobe to a temperature between −5° C. to −40° C., contacting the target tissue, organ or bone, conducting heat away from the target tissue, organ, or bone through the cryoprobe to the base of the cryoprobe and vaporizing the refrigerant through the conducted heat into the vapor mix chamber, exhausting the refrigerant vapor through the vapor mix exhaust to the refrigeration assembly, compressing the refrigerant vapor to reach a pressure and temperature required to condense, condensing the refrigerant vapor into fluid refrigerant, and cycling the fluid refrigerant through a fluid conduit into the cryoprobe chamber.

In some embodiments, this method may further include reducing the pressure and temperature of the fluid refrigerant through a throttling valve following the condensation process.

In some embodiments, during the step of conducting heat away from the tissue, organ or bone, the cryoprobe thermocouple records the temperature of the cryoprobe and reports the temperature to an external display or computing device. In yet another embodiment, during the step of recording the temperature, the external display or computing device compares recorded temperature with the pre-configured proper surgical temperatures from an electronic database and sends a command to increase the compressor rotation for additional cooling or reduce rotation to reduce cooling.

In accordance with the present invention, attention is given to the manner in which a local tumor is treated by combining incomplete tumor ablation or disruption in combination with other therapeutic modalities that stimulate the body's native immune system to elicit a response to the ablated or disrupted tumor cells. The present invention also aids in avoiding and eradicating metastatic disease by the manner in which the local tumor is treated.

One embodiment provides a method of surgical disruption of a tumor comprising the step of lowering the temperature of a portion of said tumor to between about 0° C. to about −80° C. for up to about 10 minutes.

Another embodiment comprises the step of disrupting a portion of tumor to release cells and other cellular contents may be accomplished by a large number of modalities, including, without limitation, cryoablation, ultrasound, radiation, laser, mechanical abrading, or other similar modalities of disrupting tumor cells.

Yet another embodiment of the present invention comprises the step of irradiating the tumor to the point of inducing an inflammatory response using lower than standard radiation levels of up to about 50% of standard use. This irradiation protocol can be combined with cryosurgery.

Still another embodiment of the present invention comprises the step of sequentially or concurrently administering immunological, biological and/or chemical agents in conjunction with the cryosurgery.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The terminology used herein is for the purpose of describing example embodiments only and is not intended to be limiting. For purposes of clarity, the following terms used in this patent application will have the following meanings:

The term "about" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges, is intended to mean an approximation of the value, shape or state referenced. For example, where used with a value, the term "about" is intended to include a variance of ±10% from the stated value, e.g., a stated value of 1 will also include the range of values between 0.9 and 1.1.

The term "substantially" is intended to mean a quantity, property, or value that is present to a great or significant extent and less than, more than or equal to totally. For example, substantially vertical may be less than, greater than, or equal to completely vertical.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical, biomedical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the term "therapeutically effective amount" means that amount of a substance, energy, force, or other thing administered to a body that is sufficient to elicit the desired biological or medicinal response in patients. Therefore, a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, the term "optionally" means that the subsequently described event or circumstance may or may not occur, and that the description includes instances where said event or circumstance occurs and instances in which it does not.

As used herein, the term "ablation" is intended to encompass multiple modalities of disrupting tumors and tumor cells including, without limitation, cryosurgery, ultrasound, radiofrequency (RF), photodynamic therapy, laser, mechanical abrading, biological, chemical, or pharmacological modalities. Reference to any specific modality, e.g., cryoablation, made herein is intended to be exemplary of one possible ablation modality unless the context specifically expresses otherwise.

As used herein, the term "fluid" is intended to mean any substance that deforms continuously when subjected to a shear stress, no matter how small and includes, without limitation, liquids, gases, suspensions, slurries, and gels, unless the context specifically expresses otherwise.

As used herein, the term "high temperature" is intended to mean a relatively more positive temperature, e.g., −80 degrees Celsius is a high temperature relative to −150 degrees Celsius.

As used herein, the term "low temperature" is intended to mean a relatively more negative temperature, e.g., −150 degrees Celsius is a low temperature relative to −80 degrees Celsius.

Figure 1:
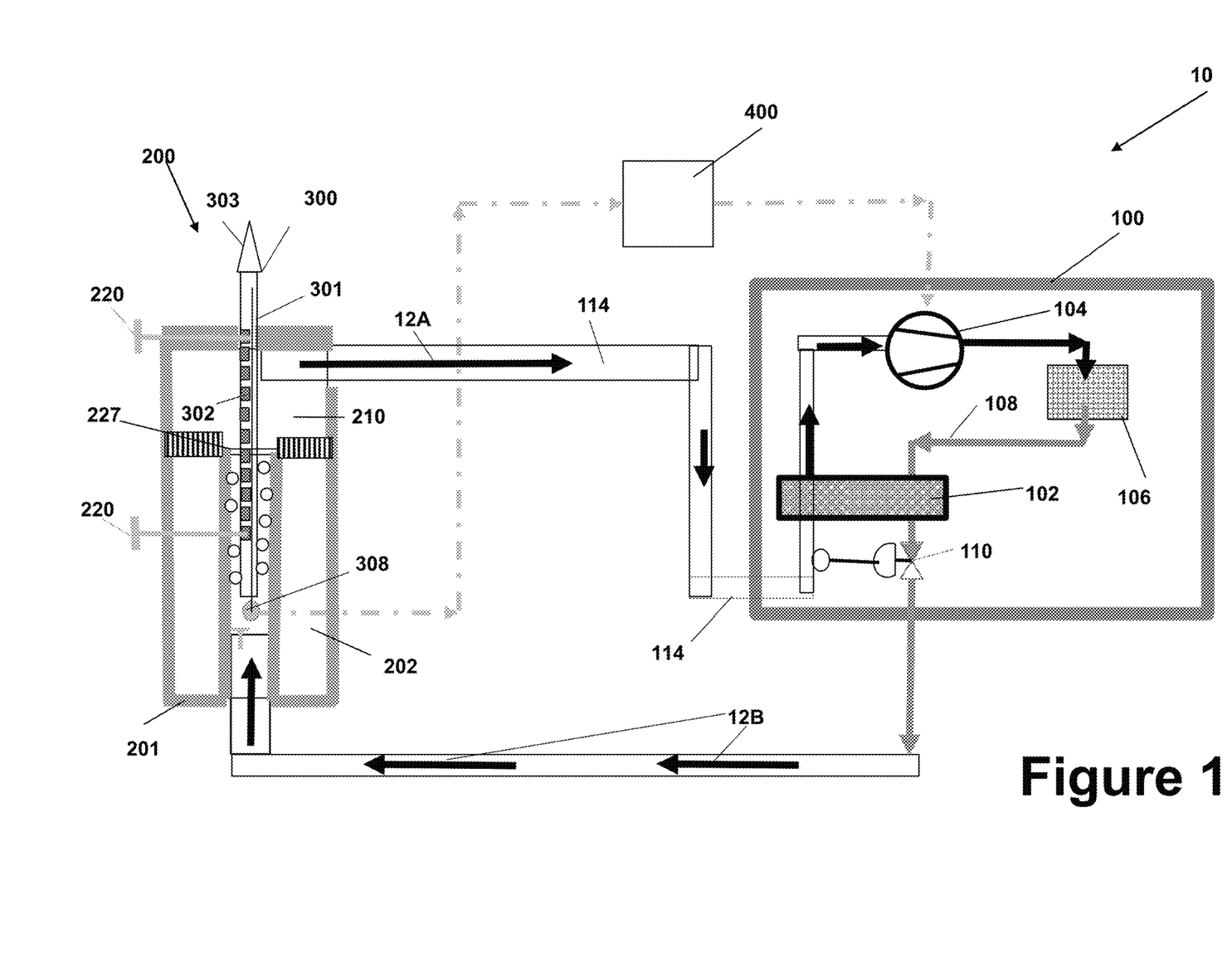
FIG. 1 is an example schematic of an embodiment of the cryosurgery system.

With reference to FIG. 1, a first embodiment of the system 10 comprises a refrigeration assembly 100, operator cooling probe 200 having a cryoprobe 300, and fluid refrigerant 12B configured to vaporize to a vapor phase refrigerant 12A when exposed to in vivo temperature conditions. In some embodiments, the system further comprises a display unit or computing device 400 communicatively coupled to the cryoprobe 300 and configured to monitor and display temperatures at the cryoprobe 300 operably communicate with the cooling or refrigeration assembly 100.

The cooling or refrigeration assembly 100 comprises a vapor intake conduit 114 configured to relay refrigerant vapors 12A from the operator cooling probe 200 through a sub-cooling device 102, through a compressor 104, through a condenser 106 configured to condense the refrigerant vapors into fluid, cycle the fluid 12B through a fluid conduit 108, through the sub-cooling device 102, and out to the operator cooling probe intake 115. In some embodiments, the refrigeration assembly 100 further comprises a throttling valve 110 configured reduce the pressure and temperature of the fluid refrigerant 12B prior to cycling to the operator cooling probe 100. In other embodiments, the system 10 may further comprise a fan (not shown) coupled to, or as part of, the condenser 106.

In some embodiments, and as an example, the operating parameters of the refrigeration assembly and system are as follows: the fluid refrigerant 12B comprises R-134A, the cooling power Q required by the system 10 may be 40W, the evaporating temperature (lowest temperature at the operator cooling probe 200 freezing tip 303) To is −40° C., the condensing temperature (the saturation temperature of the refrigerant at the pressure reached by the vapors after compression) Tc is 40° C., and the temperature of the cooling air over the condenser Tcooling_air may be 30° C. The refrigerant mass flow rate M0 through the system 10 may be 0.027×E−3 kg/s, power of the compressor P may be 19.28W having an efficiency of 0.7, the condensing power Qc may be 59.3W, and the coefficient of performance may be 2.07. The condensing power may be approximately 32W and the compressor may have refrigeration powers ranging from 20W to 100W. One of skill in the art will recognize that these operating parameters may vary based on the variation in fluid refrigerant 12B and compressor/condenser hardware, and desired cryoprobe temperatures.

Figures 2, 3, 4:
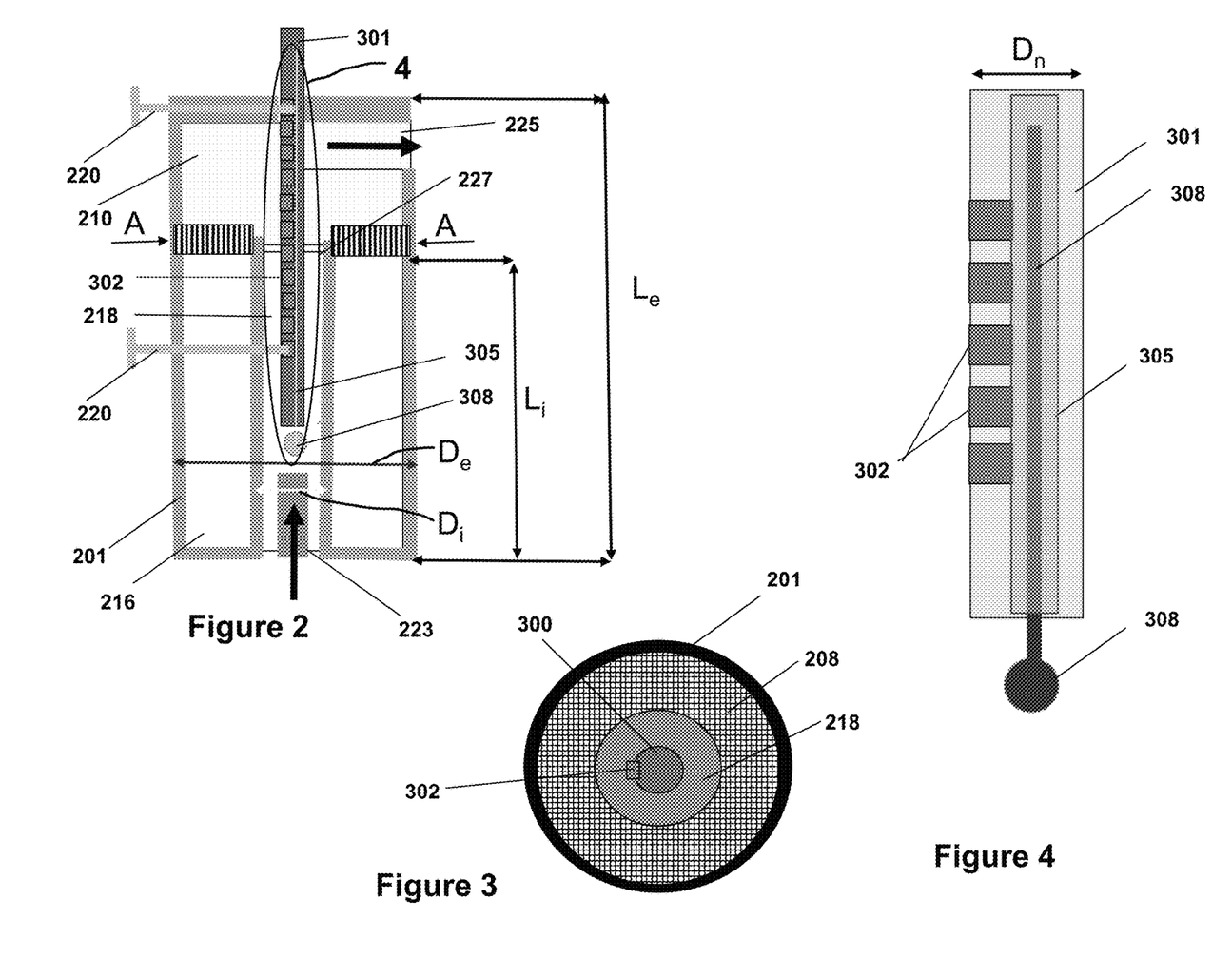
FIG. 2 is an exemplary schematic of the cryoprobe.
FIG. 3 is a cross-sectional view taken along conduit A-A of FIG. 2.
FIG. 4 is an enlarged view of the cryoprobe taken along circle 4 of FIG. 3.

In one aspect of the invention as shown in greater detail in FIG. 2, the operator cooling probe 200 comprises a housing 201, and defined within housing 201 are a fluid chamber 216, an excess fluid chamber 218, a vapor chamber 210, a fluid inlet 223 communicating with the fluid chamber 216, a vapor outlet 225 in communication with the vapor chamber 210, and a sealed opening 227 which accommodates the cryoneedle 300 to be engaged with the housing 201 in a fluidly sealed fashion. The refrigerant fluid portion of the housing 201 may be generally toroidal in shape with the excess fluid chamber 218 being centrally positioned and the fluid chamber 216 being positioned circumferentially about the excess fluid chamber 218. The housing 201 has an exterior diameter De corresponding to an outer diameter of the fluid chamber 216 and an inner diameter Di corresponding to an inner diameter of the excess fluid chamber 218, which is the inner diameter of the excess fluid chamber 218 and the outer diameter of the main refrigerant fluid chamber 216, a chamber length Li, and an operator cooling probe length Le.

The respective diameters De and Di may be optimized for refrigerant mass flow rate M0. Mass flow rate for the fluid may be calculated as follows $M0=\pi(\rho i)((Di)^2/4)) Vi$, wherein Vi is the velocity of the of the refrigerant at fluid refrigerant intake 204, $\rho i$ is the refrigerant fluid density. As such, Di may be calculated as follows: $Di=sqrt((4M0)/(\pi\rho i V_i))$. In the Example above using R-134 the refrigerant, Di=sqrt ((1.08E−03)/889.876))=0.0011 m=1.1 mm. To account for design margin, Di may be an additional 5 mm. Mass flow rate for the vapor may be calculated as follows: $M0=\pi(\rho v)((D_e)^2/4)) V_v$, wherein $V_v$ is the refrigerant vapor velocity at the vapor exhaust 212, and $\rho v$ is the vapor density. As such, De may be calculated as follows $De=sqrt((4M0)/(\pi\rho i V_v))$. In the Example above using R-134 the refrigerant, De=sqrt ((4×0.27E−3 kg/s)/(3.14×2.7777 kg/m3×3 m/s))=sqrt ((1.08E−03)/26.16))=0.0064 m=6.4 mm. To account for design margin, De may be an additional 5 mm. In this example, the Li may be approximately 14 cm and the Le may be approximately 18 cm. Additionally, in this example, the cryoprobe 300 may have a length of 25 cm, wherein up to 15 cm of the length can be extended outside of the operator cooling probe 200 or in some embodiments up to 9 cm of length can be extended outside the operator cooling probe 200. The cryoprobe 300 may also have a diameter of 3 mm to fit within the Di.

In some embodiments, as shown in FIGS. 1, 2, and 4, the cryoprobe 300 is configured as an elongate member 301 having at least an end tip 303 which is thermally conductive and configured to engage tissue. The cryoneedle 300 may further include an internal bore 305 into which a thermocouple 308 may be engaged. Thermocouple 308 monitors the temperature of the cryoprobe 300 and outputs temperature data to computer 400 and allows the operator to monitor and adjust the cryoneedle 300 temperature as desired.

Fixation adjustment points 302 may be disposed along a length of the elongate member 301 of the cryoprobe 300 and configured to engage with a fastener 220 coupled the operator cooling probe 200 to adjust the position of the cryoneedle 300 relative to the housing 201. In this embodiment, the cryoprobe tip 303 may be extended away from, or retracted into, the body of the operator cooling probe 200 and be fixed in position through the fasteners 220 and fixation adjustment points 306. In some embodiments the fixation adjustment points may be needle holes 306 and the fasteners may be retractable fixation pins 220, whereas in some embodiments the fastener may be a clamp (not shown) configured to hold the needle body 302 and predefined portions.

In additional embodiments, an optical sensor or imaging device may be operably coupled to the operator cooling probe 200 or cryoprobe 300, such as, for example, a fiber optic camera (not shown) communicatively coupled with the display or computing device 400 configured to relay magnified visual data of the target organ or tissue, and either relay that image/video to the display or computing device 400.

In yet another aspect of the invention, the computing device 400 communicatively coupled to the thermocouple 308 and/or imaging device further comprises an operating system and graphical user interface pre-configured or customizable with temperature configurations required for selected surgeries. In this embodiment, the system 10 may alert the user if the temperature is too high or too low for the particular surgery and automatically adjust the compressor or needle position or prompt the user to adjust the compressor or adjust the needle position within the operator cooling probe 200 to attain the proper temperature.

In some embodiments of the system, the refrigerant 12A, 12B comprises R-134a. R-134a, or 1,1,1,2-Tetrafluoroethane (also known as norflurane (INN), Freon 134a, Forane 134a, Genetron 134a, Florasol 134a, Suva 134a, or HFC-134a) is a hydrofluorocarbon (HFC) and haloalkane refrigerant with thermodynamic properties similar to R-12 (dichlorodifluoromethane) but with insignificant ozone depletion potential and a somewhat lower global warming potential (1,430, compared to R-12's GWP of 10,900). It has the formula $CH_2FCF_3$. One of ordinary skill in art would recognize that alternative refrigerants can be used and include, but are not limited to, R-12, R-22, R-152, HFO-1234YF, R-1143A, R-142B, R-143A, HFO-1234ze, HC-290, HC-600a, R-513A, and R-450A.

The refrigeration assembly 100 may operate by vapor compression refrigeration cycle, may operate using a Stirling cycle cooler, fluid compression/expansion refrigeration systems, thermoelectric or other cooling or refrigeration systems as are known in the refrigeration and heat-exchange arts.

In operation, a method of using the cryosurgery system 10 comprises the steps of cycling fluid refrigerant 12B through the refrigeration assembly 100 into the operator cooling probe 200 fluid chamber 202, cooling the cryoprobe 300 to a temperature between −5° C. to −80° C. depending upon the target tissue type, contacting the target organ, tissue, or bone, conducting heat from organ, tissue, or bone through the cryoprobe 300 to the base of the cryoprobe 300 and vaporizing the refrigerant 12 through the conducted heat into the vapor mix chamber 210, exhausting the refrigerant vapor 12 through the vapor mix exhaust 212 into the refrigeration assembly 100, compressing the refrigerant vapor 12A to reach a pressure and temperature required to condense, condensing the refrigerant vapor 12A into fluid refrigerant 12B, and cycling the fluid refrigerant through a fluid conduit 108 into the operator cooling probe 200 fluid chamber 202. The closed loop system results in efficient use and reuse of the refrigerant 12.

In some embodiments, following the condensation process, the method may further include the steps of reducing the pressure and temperature of the fluid refrigerant through a throttling valve 110.

In other aspects of the method, during the step of conducting heat away from the organ, tissue, or bone, the cryoprobe 300 thermocouple 308 records the temperature of the cryoprobe 300 and reports the temperature to an external display or computing device 400. Further, during the step of recording the temperature, the external display or computing device 400 compares the recorded temperature with a pre-configured proper surgical temperature and sends a command to increase the compressor rotation for additional cooling or reduce rotation to reduce cooling.

One particular advantage of the inventive system is that it generates temperatures relatively higher than those typically employed in cryoablation, and it also configurable to generate the lower temperatures, e.g., down to about −185 degrees Celsius, typically employed in conventional cryoablation procedures.

The method of surgical intervention for solid tumors disclosed here is predicated on augmenting a patient's own immunological attack on the tumor. In particular, the present invention involves interventional immunological priming created by external stimulus on the body. By use of cryosurgical methods, mechanical surgical methods, radiation methods, electrical methods, biological materials, chemical agents, immunological agents, or infections agents disclosed herein, vaccination with infectious organism components, such as attenuated virus or infectious organisms cellular components, or adoptive cell therapies, the targeted tumor will be primed for a subsequent attack based on the patient's own immunological defenses and/or pharmacological protocols. Indeed, the initial external intervention involving the aforementioned physical approaches are preferably followed immediately or preceding the intervention) and over time with additional immunological and pharmacological combinations such that the patient's own immunological attack on the tumor will be enhanced.

The potential for damage to surrounding healthy tissue, i.e., the microenvironment, relative to the location of a tumor to be treated increases proportionally to the amount of applied energy to achieve disruption or destruction of the tumor. The present invention reduces both the amount and time duration of applied energy in order to reduce trauma or damage to surrounding tissue relative to the tumor such that the tumor is incompletely or sub-totally destroyed. When employed in conjunction with sequentially or concurrently administered, i.e., either prior to, after, or at the same time as the cryoablation, immunological intervention, immunomodulation and/or pharmacological intervention can achieve complete destruction of the targeted tumor as well as known or unknown satellite metastatic tissue. Furthermore, employing methods of lesser energy utilization also means that such tools for effecting treatment can be more compact, less invasive and, typically, of lesser cost than conventional tools.

Cryosurgical procedures today generally apply a freezing source that will remove heat from tissue to a level of about −180° C. for a period of about 5 minutes to about 20 minutes. The cryosurgery method of the present invention applies a freezing source that removes heat from tissue being treated to a level between about −80° C. and about 0° C. for a period up to about 45 minutes without substantial involvement of the microenvironment.

In a useful approach for employing the method of the present invention, one can treat a tumor by inserting a temperature probe coupled to a digital thermometer that can read to a level below the aforementioned range, e.g., less than −80° C. With the temperature probe in place, one can apply the freezing medium until a desired temperature is reached in the tumor tissue as measured by the temperature probe. Independent probes measuring temperature can be inserted in different strategic locations. By monitoring changes in the targeted tissue, such as by visualizing the tissue, ultrasound, or other appropriate imaging modalities, warmer temperatures than the minimum temperature detectable by the temperature probe are used.

For the present invention, the temperature of the target tumor tissue is reduced to between about −20° C. to about −45° C. for a period of from about one minute to about 10 minutes. In another embodiment, the temperature of the target tissue is reduced to a level of between about −25° C. to about −45° C. for a period of from about 1 minute to about 10 minutes in repeated cycles.

In another embodiment, one reduces the temperature of the target tissue to a level of between about −25° C. and about −45° C. for a period of about 30 seconds, or about 45 seconds, or about one minute, or about 1½ minutes, or about 2 minutes, or about 2½ minutes, or about 3 minutes, or about 3½ minutes, or about 4 minutes, or about 4½ minutes, or about 5 minutes, or about 5½ minutes, or about 6 minutes, or about 6½ minutes, or about 7 minutes, or about 7½ minutes, or about 8 minutes or about 8½ minutes, or about 9 minutes, or about 9½ minutes, or about 10 minutes. In another embodiment, one reduces the temperature of the target tissue to a level of between about −30° C. and about −40° C. for a period of about 30 seconds, or about 45 seconds, or about one minute, or about 1½ minutes, or about 2 minutes, or about 2½ minutes, or about 3 minutes, or about 3½ minutes, or about 4 minutes, or about 4½ minutes, or about 5 minutes, or about 5½ minutes, or about 6 minutes, or about 6½ minutes, or about 7 minutes, or about 7½ minutes, or about 8 minutes or about 8½ minutes, or about 9 minutes, or about 9½ minutes, or about 10 minutes. In another embodiment, one reduces the temperature of the target tissue to a level of between about −35° C. and about −40° C. for a period of about 30 seconds, or about 45 seconds, or about one minute, or about 1½ minutes, or about 2 minutes, or about 2½ minutes, or about 3 minutes, or about 3½ minutes, or about 4 minutes, or about 4½ minutes, or about 5 minutes, or about 5½ minutes, or about 6 minutes, or about 6½ minutes, or about 7 minutes, or about 7½ minutes, or about 8 minutes or about 8½ minutes, or about 9 minutes, or about 9½ minutes, or about 10 minutes.

In another embodiment, one freezes the target tissue using a cryosurgical probe as known in the art to a level of between about −70° C. to about −80° C., or between about −60° C. and about −70° C., or between about −50° C. and about −60° C., or between about −40° C. and about −50° C., or between about −30° C. and about −40° C., or between about −20° C. and about −30° C., or between about −10° C. and about −20° C., or between about 0° C. and about −10° C.; or one freezes the target tissue to a temperature within the range of about 0° C. to about −80, e.g., to about 75° C., or r about −65° C., or about −60° C., or about −55° C., or about −50° C., or about −45° C., or about −40° C., or about −35° C., or about −30° C., or about −25° C., or about −20° C., or about −15° C., or about −10° C., or about −5° C., or about 0° C.

In this embodiment, the freezing of tissue is accomplished for a period of between about 1 minute and about 5 minutes, or between about 5 minutes and about 15 minutes, or between about 15 minutes and about 25 minutes, or between about 25 minutes and about 35 minutes, or between about 35 minutes and about 45 minutes; or the freezing of tissue is accomplished for a period of about 1 minute, or for a period of about 5 minutes, or for a period of about 10 minutes, or for a period of about 15 minutes, or for a period of about 20 minutes, or for a period of about 25 minutes, or for a period of about 30 minutes, or for a period of about 35 minutes, or for a period of about 40 minutes, or for a period of about 45 minutes, or for a period of about 50 minutes.

In another embodiment of the present invention, one can disrupt cells of a targeted tumor by exposing it to radiation at levels below that employed in standard current radiation therapy, but resulting in an inflammatory response.

Each of the above-stated applications of energy results in disruption of cells, i.e., cellular lysis, but itself does not destroy the entire tumor tissue. Indeed, it is an element of the present invention that complete destruction of the tumor is to be avoided in this initial part of the treatment. By partially destroying the tumor, cellular content spillage products from the destroyed cells are released from the tumor cells as they are lysed. The cellular content spillage products stimulate biochemical signals that prime the host's native immune system to seek out and destroy what remains of the tumor. Utilizing less aggressive treatments requires delivery methods that are not only themselves less complex and less expensive, but that are less likely to create unintended harm to neighboring healthy tissue of the microenvironment.

The tumor is ablated in a manner that releases cellular content from the ablated tumor cells. The cellular contents include antigens and other substances that are presented to the patient's native immune system in the microenvironment carried through the lymphatic system to lymph nodes for recognition and cellular response by the immune system, thereby training immune system to attack and eliminating the cancer cells. By disrupting the tumor cells, the body is alerted to recruit immune cells to the site of the tumor. This specific tumor ablation in conjunction with immunotherapy initiate the abscopal effect on local and systemic tumor cells and provides the immune system with "memory" to enable eradicating post therapeutic surfacing cancer cells in different locations. Complete destruction, which is undesirable, of the tumor will deprive the tumor microenvironment or the cellular substances needed to eradicate the remaining primary tumor or other metastatic cells. The abscopal effect may be further enhanced by conducting a second round of cryoablation after immunotherapy to boost the available tumor cellular contents to react with the immunotherapy. It will be understood by those skilled in the art that multiple successive rounds of cryoablation and/or immunotherapy and/or drug therapy are contemplated by the present invention.

In the case of cryosurgery, the commonly employed nitrogen- or argon-based machine can be replaced with a much smaller, motor driven cryosurgical machine, such as one based on the Stirling pump constructed in accordance with R. Radebaugh, *J. Phys.: Condens. Matter*, Vol. 21, 164219 (2009); A.T.A.M. de Waele, Basic operation of cryocoolers and related thermal machines, Review article, *Journal of Low Temperature Physics*, Vol. 164, pp. 179-236, (2011), DOI: 10.1007/s10909-011-0373-x; T. Kuriyama, et al., *Advances in Cryogenic Engineering* 35B, 1261 (1990); and W. E. Gifford and R. C. Longsworth, *Advances in Cryogenic Engineering* 11, 171 (1966). Nonetheless, one can use any cooling/freezing machine using common refrigeration gasses in lower pressure. One can use conductive metals to bring cooling to the tumor. One can inject solutions the bring cooling to the tumor via needle injection or through a dilated tract housing a tube. One can use any freezing machine currently used today for cryosurgery in combination with the parameters of temperature and time set forth above to employ the method of the present invention. Cryosurgery apparatuses that do not employ liquid nitrogen tend to be less cumbersome, safer and cheaper and are preferred. The following examples will facilitate a more thorough understanding of the present invention.

Example 1

The following is an exemplary protocol for cancer treatment that employs the cryosurgery system of the present invention.

Prior to external energy intervention, a hormonal blockade is applied to assist in facilitating the downstream immunological response post energy application. The hormonal blockade is administered initially between one and three weeks before surgery and is continued during and after surgery.

The tumor is visualized by an imaging modality such as by ultrasound, CT scan, MRI or PET scan. At least a portion of the tumor is then treated by cold application using cryosurgical probes as known in the art. Where MM is employed as the imaging modality, the cryosurgical probes will, of course, be MM compatible. Temperature is measured and changes are noted in the tumor.

Checkpoint inhibitors may be injected in the vicinity of the tumor or in the tumor or in the vein for systemic approach, or through an artery feeding the tumor to direct the effect to the tumor. Immune modulators, i.e., granulocyte-macrophage colony-stimulating factor (GM-CSF), are administered daily for a period of two weeks and a two to three times a week thereafter. The routine doses of GM-CSF already approved by United States Food and Drug Administration ("FDA") are given.

A light dosing of chemotherapy is optionally in the first one to two weeks post-surgery, using, for example, 25 mg cyclophosphamide orally daily.

Follow up in one month is scheduled to evaluate the response of the treatment. If necessary, cryosurgery is repeated followed by continued immune modulation using GM-CSF.

Electroporation may also be used in the tumor and the vicinity of the tumor that was not destroyed or in the surrounding tissue. Electroporation may be concurrent with, prior to or subsequent to the cryoablation.

Example 2

Another exemplary treatment protocol is for metastatic disease in bone that employs the cryosurgery system and method of present invention.

Where the metastatic disease is in the bone, a cryoprobe with a flat head or needle is applied after the skin about the lesion is incised. The current standard of care is to give cryoablation on the bone only for palliation to relieve the pain. By gentle cryoablation of the exposed tumor followed by immunomodulation, one can extend the palliation to a curative treatment for disease located elsewhere in the body or residual cancer in the bone, in the area of the initial freezing. That is, the palliative procedure turns into therapeutic intervention on other areas where the cancer is distant to the tumor in the bone that was frozen. Ablation of bone cancer may be performed under imaging, such as by radiological imaging such as X-ray or fluoroscopy.

Example 3

Cryoablation is applied to a primary bone tumor or bone metastatic tissue for purposes of palliation of pain. Local or systemic immunomodulators may be administered to the patient concurrently or after ablation to inhibit growth of the cancer cells. For example, it is known that administration of phosphodiesterase-5 inhibitor, for example sildenafil citrate (VIAGRA Pfizer, New York, N.Y.), downregulates expression of arginase and inducible nitric oxide synthase expression by myeloid-derived supressor cells (MDSCs), thereby inhibiting their suppressive function in growing tumors. See, e.g., Grabrilovich, D. I., et al, *Nat Rev Immunol.* 2009 March; 9(3): 162-174. doi: 10.1038/nri2506. Influenza vaccine may also be added as part of the immune therapeutic regimen.

While preferred embodiments of the present invention have been described herein, it will be obvious to those skilled in the art that such embodiments are provided by way of example only. The examples of treatment protocols are intended to be non-limiting and are only examples of the tumor type, tissue, treatment protocols or the like. Numerous variations, changes, and substitutions will now occur to those skilled in the art without departing from the invention or the definitions provided herein for clearly recording inventor's conception and embodiments thereof. It should be understood that various alternatives to the embodiments of the invention described herein may be employed in practicing the invention.

What is claimed is:

1. A cryosurgery system comprising:
    a. a refrigeration assembly having a vapor intake conduit fluidly coupled to an operator probe, a compressor, a condenser configured to condense refrigerant in a vapor state into the refrigerant in a fluid state, a sub-cooling device coupled to a vapor intake conduit and the condenser, and a throttling valve coupled to the condenser configured to reduce the temperature and pressure of the refrigerant;
    b. the operator probe having a housing, a fluid chamber, a fluid inlet communicating with the fluid chamber, a vapor chamber; a fluid outlet communicating with the vapor chamber; a fluid conduit in communication with the fluid inlet and a vapor conduit in communication with the vapor outlet;
    c. a cryoneedle operably coupled to the housing of the operator probe and in communication with the fluid inlet and the vapor chamber of the operator probe;
    d. a refrigerant contained within the fluid chamber, the vapor chamber, the fluid conduit and the vapor conduit; and
    wherein the operator probe and the refrigeration assembly are fluidly coupled in a closed loop configured to cycle the refrigerant in a fluid state from the refrigeration assembly to the operator probe and further configured to cycle the refrigerant in a vapor state from the operator probe to the refrigeration assembly.

2. The cryosurgery system of claim 1 wherein the operator probe further comprises:
    a. a fluid refrigerant intake fluidly coupled to the refrigeration assembly;
    b. a fluid refrigerant chamber fluidly coupled to the fluid refrigerant intake;
    c. a vapor fluid separator member coupled to the fluid refrigerant chamber;
    d. a vapor mix chamber coupled to the vapor fluid separator member;
    e. a vapor exhaust conduit fluidly coupled to the vapor mix chamber and the refrigeration assembly; and
    an operator probe body and operator probe tip at a distal end of the cryoprobe body, the cryoprobe body partially disposed within the fluid refrigerant chamber, partially disposed within the vapor mix chamber, and the partially extending outside the cryoprobe body.

3. The cryosurgery system of claim 2 wherein the fluid refrigerant chamber further comprises a main refrigerant fluid chamber configured to accommodate the cryoprobe body, and an excess fluid chamber configured to store excess refrigerant.

4. The cryosurgery system of claim 3 wherein the cryoprobe body is hollow.

5. The cryosurgery system of claim 4 wherein the cryoprobe further comprises attachment points configured to accept an attachment fastener configured to constrain a position of the cryoprobe.

6. The cryosurgery system of claim 2 wherein the cryoprobe further comprises at least one thermocouple disposed inside or outside the cryoprobe body, the at least one thermocouple further coupled to an external display or computing device configured to read and display the temperature at the at the at least one thermocouple.

7. The cryosurgery system of claim 6 wherein the computing device is communicatively coupled to a database comprising preprogrammed needle temperatures for pre-identified surgeries.

8. The cryosurgery system of claim 7 wherein the computing device is configured to provide an alert if the temperature of the cryoprobe deviates from the preprogrammed needle temperature for the pre-identified surgery.

9. The cryosurgery system of claim 7 wherein the computing device is communicatively coupled to the refrigeration assembly and is configured to adjust the temperature of the refrigerant to match the preprogrammed needle temperature for the pre-identified surgery, or the computing device is communicatively coupled to the cryoprobe and is configured to adjust the position of the cryoprobe within the operator cooling probe.

10. A cryosurgical apparatus, comprising:
  a. a thermal probe configured to deliver cooling energy to tissue adjacent a tip of the thermal probe, the thermal probe further comprising a housing, a fluid chamber, a fluid inlet communicating with the fluid chamber, a vapor chamber, a fluid outlet communicating with the vapor chamber, a fluid conduit in communication with the fluid inlet and a vapor conduit in communication with the vapor outlet, and a cryoneedle having a distal end thereof that extends through the vapor chamber and into an excess fluid chamber of thermal probe;
  b. a heat exchanger coupled to a source of a cooling fluid, the heat exchanger being operably coupled to the thermal probe to communicate the cooling fluid to the thermal probe;
  c. a temperature sensor operably coupled to the thermal probe capable of measuring a temperature at the tip of the thermal probe; and
  d. a controller to control a temperature at the tip of the thermal probe.

11. The cryosurgical apparatus of claim 10, wherein the controller further comprises a temperature regulator controlling the temperature of the tip of the thermal probe to between about 0° C. and −80° C.

12. The cryosurgical apparatus of claim 11, wherein the controller further comprises a clock limiting a time of application of cooling energy to the thermal probe to maintain the temperature of the tip between about 0° C. and −80° C. for a period of time between about 1 to about 10 minutes.

13. A method of using a cryosurgery system having a refrigeration assembly, a cryoprobe, and a refrigerant, wherein the cryoprobe and the refrigeration assembly are fluidly coupled in a closed loop configured to cycle the refrigerant in a fluid state from the refrigeration assembly to the cryoprobe and further configured to cycle the refrigerant in a vapor state from the cryoprobe to the refrigeration assembly, the method comprising the steps of:
  a. cooling the refrigerant in a fluid state;
  b. cycling the refrigerant in a fluid state from the refrigeration assembly through a fluid conduit fluidly coupled to a fluid refrigerant intake of the cryoprobe, through the a fluid refrigerant intake into a fluid refrigerant chamber, the fluid refrigerant chamber having a cryoprobe having a cryoprobe body and cryoprobe tip at a distal end, the cryoprobe body partially disposed within the fluid refrigerant chamber;
  c. cooling the cryoprobe;
  d. conducting heat through the cryoprobe tip to the refrigerant;
  e. vaporizing the refrigerant into a vapor mix chamber of the cryoprobe; and
  f. cycling the vaporized refrigerant through a vapor exhaust of the vapor mix chamber to the refrigeration assembly fluidly coupled to the vapor exhaust
  g. cycling the vaporized refrigerant through a sub-cooling device of the refrigeration assembly;
  h. cycling the vaporized refrigerant through a compressor;
  i. compressing the vaporized refrigerant to reach a pressure and temperature required to condense; and
  j. condensing the vaporized refrigerant through a condenser of the refrigeration assembly into a fluid refrigerant;
  k. cycling the fluid refrigerant through a throttling valve to reduce temperature and pressure of the fluid refrigerant; and
  l. cycling the fluid refrigerant back through the cryoprobe.

14. The method of claim 13 further comprising the steps of:
  a. recording the temperature of the cryoprobe through at least one thermocouple coupled to the cryoprobe; and
  b. relaying the recorded temperature to an external display or computing device communicatively coupled to the at least one thermocouple.

15. The method of claim 14 further comprising the steps of comparing the temperature of the cryoprobe to an electronic database comprising preprogrammed needle temperatures for pre-identified surgeries and the computing device communicatively coupled to the refrigeration assembly, adjusting the temperature of the refrigerant through adjusting a compressor of the refrigeration assembly to match the preprogrammed needle temperature for the pre-identified surgery, or the computing device communicatively coupled to the cryoprobe, adjusting the position of the cryoprobe within the operator cooling probe.

16. A method of claim 13, further comprising the step of treating a tumor by applying the cryoprobe cooled to a temperature between about 0 to about −80 degrees Centigrade to the tumor for a period of time sufficient to substantially disrupt the tumor and administering an immunomodulation agent tumor treatment prior to, concurrently with, or subsequent to the step of applying the cryoprobe.

* * * * *